(12) United States Patent
Grant et al.

(10) Patent No.: US 7,309,314 B2
(45) Date of Patent: Dec. 18, 2007

(54) METHOD FOR PREDICTING APNEA-HYPOPNEA INDEX FROM OVERNIGHT PULSE OXIMETRY READINGS

(75) Inventors: Brydon J. B. Grant, East Amherst, NY (US); Jacek Dmochowski, Williamsville, NY (US)

(73) Assignees: U.S. Department of Veterans Affairs, Washington, DC (US); University of New York, Amherst, NY (US)

( * ) Notice: Subject to any disclaimer, the term of this patent is extended or adjusted under 35 U.S.C. 154(b) by 341 days.

(21) Appl. No.: 10/947,983

(22) Filed: Sep. 23, 2004

(65) Prior Publication Data

US 2005/0131283 A1    Jun. 16, 2005

Related U.S. Application Data

(60) Provisional application No. 60/505,288, filed on Sep. 23, 2003.

(51) Int. Cl.
*A61B 5/00* (2006.01)
(52) U.S. Cl. .................. 600/529; 600/323; 600/484
(58) Field of Classification Search ................ 600/300, 600/301, 323, 324, 529, 533, 544, 546, 587, 600/508, 509, 534, 537, 481; 128/898
See application file for complete search history.

(56) References Cited

U.S. PATENT DOCUMENTS

| | | | |
|---|---|---|---|
| 4,129,125 A | 12/1978 | Lester et al. | |
| 4,715,367 A | 12/1987 | Crossley | |
| 4,802,485 A | 2/1989 | Bowers et al. | |
| 4,862,144 A | 8/1989 | Tao | |
| 5,046,491 A | 9/1991 | Derrick | |
| 5,150,414 A | 9/1992 | Ng | |
| 5,245,995 A | 9/1993 | Sullivan et al. | |
| 5,353,788 A | 10/1994 | Miles | |
| 5,385,144 A | 1/1995 | Yamanishi et al. | |
| 5,404,885 A | 4/1995 | Sheehan et al. | |
| RE35,122 E | 12/1995 | Corenman et al. | |

(Continued)

FOREIGN PATENT DOCUMENTS

WO    WO 87/02577    5/1987

(Continued)

OTHER PUBLICATIONS

Blackshear, et al., *Nocturnal Dyspnea and Atrial Fibrillation Predict Cheyne-Stokes Respirations in Patients with Congestive Heart Failure*, Arch Intern Med, Jun. 26, 1995, vol. 155, pp. 1297-1302.

(Continued)

*Primary Examiner*—Charles A. Marmor, II
*Assistant Examiner*—Karen E Toth
(74) *Attorney, Agent, or Firm*—Hodgson Russ LLP

(57) ABSTRACT

The present invention provides a predictive tool for predicting Apopnea Hypopnea Index (AHI) in the diagnosis of Obstructive sleep apnea (OSA). The predictive tool is developed by recording pulse oximetry readings, obtaining delta index, oxygen saturation times and oxygen desaturation events from the oximetry readings. A multivariate non-parametric analysis and bootstrap aggregation is performed to obtain predictive models which can be used to predictive AHI in an individual and to classify an individual as having or not having OSA.

24 Claims, 4 Drawing Sheets

U.S. PATENT DOCUMENTS

| | | | |
|---|---|---|---|
| 5,515,865 | A | 5/1996 | Scanlon |
| 5,522,382 | A | 6/1996 | Sullivan et al. |
| 5,522,862 | A | 6/1996 | Testerman et al. |
| 5,535,739 | A | 7/1996 | Rapoport et al. |
| 5,575,285 | A | 11/1996 | Takanashi et al. |
| 5,605,151 | A | 2/1997 | Lynn |
| 5,671,733 | A | 9/1997 | Raviv et al. |
| 5,684,460 | A | 11/1997 | Scanlon |
| 5,689,247 | A | 11/1997 | Welner |
| 5,704,345 | A | 1/1998 | Berthon-Jones |
| 5,724,983 | A | 3/1998 | Selker et al. |
| 5,769,084 | A | 6/1998 | Katz et al. |
| 5,796,340 | A | 8/1998 | Miller |
| 5,797,852 | A | 8/1998 | Karakasoglu et al. |
| 5,803,066 | A | 9/1998 | Rapoport et al. |
| 5,839,438 | A | 11/1998 | Graettinger et al. |
| 5,844,996 | A | 12/1998 | Enzmann et al. |
| 5,853,005 | A | 12/1998 | Scanlon |
| 5,953,713 | A | 9/1999 | Behbehani et al. |
| 6,083,173 | A | 7/2000 | Grant et al. |
| 6,142,950 | A | 11/2000 | Allen et al. |
| 6,171,258 | B1 | 1/2001 | Karakasoglu et al. |
| 6,213,955 | B1 | 4/2001 | Karakasoglu et al. |
| 6,223,064 | B1 | 4/2001 | Lynn et al. |
| 6,290,654 | B1 | 9/2001 | Karakasoglu |
| 6,580,944 | B1 | 6/2003 | Katz et al. |
| 6,594,518 | B1 | 7/2003 | Benaron et al. |
| 6,839,581 | B1* | 1/2005 | El-Solh et al. ............... 600/324 |
| 6,942,626 | B2 | 9/2005 | Salisbury et al. |
| 7,153,264 | B2 | 12/2006 | Katz et al. |
| 2002/0002327 | A1 | 1/2002 | Grant et al. |
| 2002/0165462 | A1* | 11/2002 | Westbrook et al. ......... 600/529 |
| 2007/0129643 | A1* | 6/2007 | Kwok et al. ................ 600/529 |

FOREIGN PATENT DOCUMENTS

| | | |
|---|---|---|
| WO | WO 89/07701 | 8/1989 |
| WO | WO 92/17019 | 10/1992 |
| WO | WO 97/40748 | 11/1997 |
| WO | WO 00/19895 | 4/2000 |
| WO | WO 00/20047 | 4/2000 |

OTHER PUBLICATIONS

Dowdell, et al., *Cheyne-Stokes Respiration Presenting as Sleep Apnea Syndrome*, Clinical and Polysomnographic Features, Am Rev Respir Dis, Apr. 1190, vol. 141(4 Pt 1), pp. 871-879.

Hanley, et al., *Pathogenesis of Cheyne-Stokes Respiration in Patients with Congestive Heart Failure, Relationship to Arterial PCO2.* Chest, 1993, vol. 104, pp. 1079-1084.

Staniforth, et al., *Nocturnal Desaturation in Patients with Stable Heart Failure*, Heart, Apr. 1998, vol. 79(4), pp. 394-399.

Pack et al., Oscillatory Changes in Ventilation, Awake and Asleep, Concepts and Formalizations in the Control of Breathing, 1987, p. 299-311, Manchester Univ. Press.

Pack et al., Spectral Analysis of Ventilation in Elderly Subjects Awake and Asleep, J. Appl. Physiol., 1988, p. 1257-67, v.64(3), Univ. of Penn.

Pack et al., Changes in Control of Ventilation, Awake and Asleep, in the Elderly, J. Am. Geriatr. Soc., 1986, p. 533-44, v.34(7), Univ. of Penn.

Shore et al., Ventilatory and Arousal Patterns During Sleep in Normal Young and Elderly Subjects, J. Appl. Physiol., 1985, p. 1607-15, v.59(5), Univ. of Penn.

Katz et al., A Practical Nonlinear Method for Detection of Respiratory and Cardiac Dysfunction in Human Subjects, SPIE, 1995, p. 189-206, v.2612, Philadelphia.

U.S. Appl. No. 60/211,696, filed Jun. 14, 2000, Wallach.

ApneaScreen 1 from CNS, your partner of choice. 1992. *CNS, INC.*

ASDA Report, 1992. EEG Arousals: Scoring Rules and Examples, A Preliminary Report from the Sleep Disorders Atlas Task Force of the American Sleep Disorders Association. *Sleep* 15: 173-175.

Barbe, et al., 2001. Treatment with Continuous Positive Airway Pressure is Not Effective in Patients with Sleep Apnea but No Daytime Sleepiness. *Annals of Internal Medicine* 134 (11): 1015-1023.

Baxt, W., 1991. Use of an Artificial Neural Network for Diagnosis of Myocardial Infarction. *Annals of Internal Medicine* 115: 843-848.

Berger, et al., 1986. An Efficient Algorithm for Spectral Analysis of Hearth Rate Variability. *IEE Transactions on Biomedical Engineering* BME-33 (9): 900-904.

Berthon -Jones, et al., 1994. Sleep & Breathing: Therapy A Self-Adjusting CPAP Device for OSA. *Abstract from APSS 8th Annual Meeting*, Boston 334.

Breiman, et al., 1984. Classification and Regression Tress. *Wadsworth International Group*, Belmont CA.

Briskorn, C., 1995. Sleep Market Wide Awake, It's a booming market, but success in the sleep testing and therapy business depends on partnering with physicians and managed care payers. *Homecare* 97-98 and 100.

Chiner, et al., 1999. Nocturnal oximetry for the diagnosis of the sleep apnoea hypopnoea syndrome: a method to reduce the number of polysomnographies? *Thorax* 54: 968-971.

Clark, et al., 1994. Prognostic factors—Rationale and methods of analysis and integration. *Breast Cancer Research and Treatment* 32: 105-112.

CNS—ApneaScreen I. 1992, A Cost-effective solution to meet the increasing demand for portable testing. *CNS, INC.*

Crocker, et al., 1990. Estimation of the Probability of Disturbed Breathing During Sleep before the Sleep Study. *American Review of Respiratory Disease* 142 (1): 14-18.

Cummisky, et al., 1982. The Detection and Quantification of Sleep Apnea by Tracheal Sound Recordings. *AM Rev Respir Dis* 128: 221-224.

Douglas, et al., 2000. Upper Airway Resistance Syndrome Is Not a Distinct Syndrome. *American Journal of Repiratory and Critical Care Medicine* 161 (5): 1413-1416.

Douglas, et al., 1992. Clinical value of polysomnography. *Lancet* 339: 347-350.

Doyle, et al., 1994. Predicting Outcomes After Liver Transplantation. *Annals of Surgery* 219: 408-415.

Dybowslki, et al., 1996. Prediction of outcome in critically ill patients using artificial neural network synthesised by genetic algorithm. *Lancet* 347: 1146-1150.

Dyken, et al., 1996. Investigating the Relationship Between Stroke and Obstructive Sleep Apnea. *Stroke* 27 (3): 401-407.

El-Solh, et al., 2003 The Utility of Neural Network in the Diagnosis of Cheyne-Stokes Respiration. *Journal of Medical Engineering & Technology* 27 (2): 54-58.

Engleman, et al., 1999. Randomized Placebo-controlled Crossover Trial of Continuous Positive Airway Pressure for Mild Sleep Apnea/Hypopnea Syndrome. *Am J Respir Crit Care Med* 159 (2): 461-467.

Fairbanks, D., 1987. Snoring: An Overview with Historical Perspectives. *Snoring and Obstructive Sleep Apnea* 1-17.

Findley, et al., 1995. Cheyne-Stokes breathing during sleep in Patients with left ventricular heart failure. *Southern Medical Journal* 78 (1): 11-15.

Gordon, et al., 1992. An Artificial Neural Network Controller Model for Active Attenuation. *Intelligent Engineering Systems Through Artificial Neural Networks* 2: 655-660.

Granton, et al., 1996. CPAP Improves Inspiratory Muscle Strength in Patients with Heart Failure and Central Sleep Apnea. *Am J Respir Crit Care Med* 153: 277-282.

Guilleminault, et al., 1993. A Cause of Excessive Daytime Sleepiness, The Upper Airway Resistance Syndrome. *Chest* 104 (3): 781-787.

Guilleminault, et al., 1992. EEG Arousals: Scoring Rules and Examples, A Preliminary Report from the Sleep Disorders Atlas Task Force of the American Sleep Disorders Association. *Sleep* 15 (2): 173-184.

Guilleminault, et al., 2000. Upper Airway Resistance Syndrome and its Treatment. *Sleep* 23 (S4): S197-S200.

Hanly, et al., 1996. Increased Mortality Associated with Cheyne-Stokes Respiration in Patients with Congestive Heart Failure. *Am J Respir Crit Care Med* 153: 272-276.

Hart, et al., 1990. Evaluating black-boxes as medical decision aids: issues arising from a study of neural networks. *Medical Informatics* 15 (3): 229-236.

He, et al., 1988. Mortality and Apnea Index in Obstructive Sleep Apnea. *Chest* 94: 9-14.

Hiraiwa, et al., 1990. EEG Topography Recognition by Neural Networks. *IEEE Engineering in Medicine and Biology* 9 (3): 39-42.

Hoffstein, et al., 1993. Predictive Value of Clinical Features in Diagnosing Obstructive Sleep Apnea. *Sleep* 16 (2): 118-122.

Hurvich, et al., 1989. Regression and time series model selection in small samples. *Biometrika* 76 (2): 297-307.

Issa, et al., 1993. Digital Monitoring of Sleep-disordered Breathing Using Snoring Sound and Arterial Oxygen Saturation. *Am Rev Respir Dis* 148: 1023-1029.

Javaheri et al., 1995. Occult Sleep-Disordered Breathing in Stable Congestive Heart Failure. *Annals of Internal Medicine* 122 (7): 487-492.

Javaheri et al., 1998. Sleep Apnea in 81 Ambulatory Male Patients with Stable Heart Failure Types and Their Prevalences Consequences, and Presentations. *Circulation* 97 (21): 2154-2159.

Khoo, et al., 1999. Spectral Indices of Cardiac Autonomic Function in Obstructive Sleep Apnea. *Sleep* 22 (4): 443-451.

Kump, et al., 1994. Assessment of the Validity and Utility of a Sleep Symptom Questionnaire. *Am J Respir Crit Care Med* 150 (3): 735-741.

Long, et al., 1993. A Comparison of Logistic Regression to Decision-Tree Induction in a Medical Domain. *Computers and Biomedical Research* 26: 74-97.

Maislin, et al., 1994. The Prevalence of Frequent Episodes of Falling Asleep while Driving in Patients Seen at Sleep Disorders Centers. *Sleep Research* 23: 133.

Maislin, et al., 1995. A Survey Screen for Prediction of Apnea. *Sleep* 18 (3): 158-166.

Naughton, et al., 1995. Effects of Nasal CPAP on Sympathetic Activity in Patients with Heart Failure and Central Sleep Apnea. *Am. J. Respir Crit Care Med* 152 (2): 473-479.

Naughton, et al., 1993. Role of Hyperventilation in the Pathogenesis of Central Sleep Apneas in Patients with Congestive Heart Failure. *Am. Rev Respir Dis* 148 (2): 330-338.

Nieto, et al., 2000. Association of Sleep-Disordered Breathing Sleep Apnea and Hypertension in a Large Community-Based Study. *JAMA* 283 (14): 1829-1836.

Partinen, et al., 1988. Long-Term Outcome for Obstructive Sleep Apnea Syndrome Patients. 94 (6): 1200-1204.

Peppard, et al., 2000. Prospective Study of the Association Between Sleep-Disordered Breathing and Hypertension. 342: (19): 1378-1384.

Press, et al., 1989. *Numerical Recipes*, Cambridge University Press Chapter 12, 381-453.

Rechtschaffen, et al., 1968. A Manual of Standardized Technology Techniques and Scoring System for Sleep Stages of Human Subjects. Los Angeles: UCLA Brain Information Service/Brain Research Institute 204: 1-13 and figures 1-40.

Redline, et al., 1998. Improvement of Mild Sleep-disordered Breathing wiht CPAP Compared with Conservative Therapy. *Am J Respir Crit Care Med* 157 (3): 858-865.

Redline, et al., 2000. Effects of Varying Approaches for Identifying Respiratory Disturbances on Sleep Apnea Assessment. *Am J Respir Crit Care Med* 161 (2): 369-374.

Sangil and Park, 1990. Full-duplex speakerphone with acoustic and electric echo-canceller utilizing the DSP56200 cascadable adaptive FIR filter chip. *Proc. Of Midcon/90 Technical Conference on Electronic and Electrical Technology*, Dallas, TX, 295-299, Sep. 11-13.

Series, et al., 1993. Utility of Nocturnal Home Oximetry for Case Finding in Patients with Suspected Sleep Apnea Hypopnea Syndrome. *Annals of Internal Medicine* 119 (6): 449-453.

Servera, et al., 1995. Changes in Work Absenteeism in Patients with Obstructive Sleep Apnea Syndrome After Treatment. *Chest* 108 (2): 162S.

Shahar, et al., 2001. Sleep-disordered Breathing and Cardiovascular Disease Cross-sectional Results of the Sleep Heart Health Study. *Am J Respir Crit Care Med* 163: 19-25.

Shepard, et al., 1992. Hypertension, Cardiac Arrhythmias, Myocardial Infarction, and Stroke in Relation to Obstructive Sleep Apnea. *Clinics in Chest Medicine* 13 (3): 437-458.

Sin, et al., 2000. Effects of Continuous Positive Airway Pressure on Cardiovascular Outcomes in Heart Failure Patients With and Without Cheyne-Stokes Respiration. *Circulation* 102: 61-66.

Tourassi, et al., 1993. Acute Pulmonary Embolism: Artificial Neural Network Approach for Diagnosis. *Radiology* 189 (2): 555-558.

Tsai, et al., 1999. A Comparison of Apnea-Hypopnea Indices Derived from Different Definitions of Hypopnea. *Am J Respir Crit Care Med* 159: 43-48.

Vaidya, et al., 1996. Identifying Obstructive Sleep Apnea in Patients Presenting for Laser-Assisted Uvulopalatoplasty. *Laryngoscope* 106 (4): 431-437.

Viner, et al., 1991. Are History and Physical Examination a Good Screening Test for Sleep Apnea? *Annals of Internal Medicine* 115 (5): 356-359.

Weiss, et al., 1991. How to Estimate the True Performance of a Learning System. *Computer Systems That Learn* Palo Alto, CA: Morgan Kaufman 17-49.

Weiss, et al., 1991. Neural Nets. In: *Computer Systems that Learn*. Palo Alto, CA: Morgan Kaukman 81-112.

Widrow, et al., 1985. Adaptive Signal Processing. *Prentice-Hall*, New Jersey 270-301.

Wu, et al., 1993 Artificial Neural Networks in Mammography-Application to Decision Making in the Diagnosis of Breast Cancer. *Radiology* 187: 81-87.

Yamashiro, et al., 1995. Nocturnal Oximetry: Is It a Screening Tool for Sleep Disorders? *Sleep* 18 (3): 167-171.

Young, et al., 1993. The Occurrence of Sleep-Disordered Breathing Among Middle-Aged Adults. *The New England Journal of Medicine* 328 (17): 1230-1235.

* cited by examiner

METHOD FOR PREDICTING APNEA-HYPOPNEA INDEX FROM OVERNIGHT PULSE OXIMETRY READINGS

This application claims benefit of U.S. Provisional Application No. 60/505,288, filed Sep. 23, 2003, the disclosure of which is incorporated herein by reference.

FIELD OF THE INVENTION

The present invention relates generally to the field of sleeping disordered breathing. More particularly, the present invention provides a predicted tool to predict the apnea-hypopnea index.

DISCUSSION OF RELATED ART

The obstructive sleep apnea (OSA) syndrome is a major health problem affecting 2-4% of the middle-aged population. At present, polysomnography (PSG) is considered the reference standard diagnostic test for this condition (AH-CPR Publication 99-E002, February 1999). However, PSG is costly and time consuming. As a result, primary care providers may be reluctant about ordering PSG and patients unwilling to attend their tests. Overnight pulse oximetry has been proposed as a simpler alternative to PSG in the diagnosis of OSA because it is readily available, relatively inexpensive, and could potentially meet the large demand for diagnostic testing in the community. It can be easily done at home and repeated, if need be, which is not the case with a PSG even performed at home.

At present there is no definite established AHI criterion for the diagnosis of OSA with the threshold varying from 5-20 events/hour. Most clinicians will modify initiation of treatment depending on the patient's symptoms and other clinical characteristics. Recent reports suggest that even what is considered as mild sleep-disordered breathing is associated with hypertension and cardiovascular disease, and that these patients with mild disease may also benefit from continuous positive airway pressure (CPAP) therapy. A consensus statement recommended that treatment be administered if the AHI is $\geq 30$ events/hour regardless of symptoms. However, results from a recently published study do not support this recommendation since patients with an AHI of $\geq 30$/hour who did not have daytime sleepiness did not benefit from CPAP therapy. Therefore, a prediction of the actual AHI from overnight oximetry would be more clinically meaningful than a dichotomous answer to the presence of OSA, and that it would be more useful if this prediction can be computerized to eliminate the problem of interobserver and intraobserver variability.

Several quantitative indices derived from overnight pulse oximetry have been used to predict the presence of OSA. These indices include the number of oxyhemoglobin desaturation events below a certain threshold, usually 3% or 4% decline from baseline, the cumulative time spent below an oxyhemoglobin saturation of 90% (CT 90), and the delta index, a measure of the variability of the oxyhemoglobin saturation (Levy et al., Chest (1996); 109:395-99). One study has suggested that the number of desaturation events >4% as well as the 12-second delta index also predicts the response to CPAP therapy in patients with OSA (Choi et al., Respir Med (2000); 94:895-99). Although these quantitative indices appear to hold more promise than visual inspection of the overnight pulse oximetry tracing, there has been no systematic comparison of their relative utility in the diagnosis of OSA. As a result, physicians select different parameters to interpret overnight pulse oximetry results.

Most published studies utilizing these quantitative oximetry indices have been performed at a single institution. Thus, the applicability of these indices to the general population remains uncertain. In addition, their accuracy has been validated using different threshold values of the AHI due to a lack of established criterion for the diagnosis of OSA. In practice, most physicians tend to modify the initiation of treatment for OSA depending on the patient's symptoms and clinical characteristics. Prediction of the actual AHI from overnight pulse oximetry is likely to be more useful than using threshold values to define OSA that has been customary in all but a few studies involving pulse oximetry.

SUMMARY OF THE INVENTION

The present method provides a method for predicting Apnea Hypopnea Index (AHI) using the predictive tool described herein. Based on the predicted AHI, an individual can be diagnosed as having or not having obstructive sleep apnea.

The predictive tool is obtained by identifying patients having obstructive sleep apnea; determining actual AHI in the patients using standard methods; obtaining pulse oximetry recordings from the patients; determining a set of indices from the pulse oximetry readings such as delta index, time spent at selected oxygen saturation levels, and oxygen desaturation events; performing random sampling with replacement to generate different data sets; performing multivariate non-parametric analysis in the data sets to generate prediction models; obtaining a predictive AHI value for each patient corresponding to each prediction model; and comparing the predictive AHI value to actual AHI value for each patient to provide weight to each prediction model. The prediction models and the weight assigned to each model provides a predictive tool for determining AHI in an individual.

In another embodiment, a method is provided for determining AHI in an individual. For the determination of the AHI, pulse oximetry readings are obtained from the individual, and a set of indices determined comprising delta index, time spent at selected oxygen saturation levels and oxygen desaturation events. This data is then input into the prediction models and based on the weight assigned to each prediction model a weighted average (final value) is determined for a AHI value for that individual. Based on this final value of AHI, a classification of the individual as having or not having OSA can be made.

In another embodiment, a software storage device is provided having thereon a computer readable code for executing steps to determine the AHI in an individual as described herein.

In another embodiment, the predictive tool further utilizes a set of indices for generating predictive models selected from the group consisting of data obtained by standard overnight PSG with recordings of electroencephalogram (EEG), electro-oculogram, submental and bilateral leg electromyograms, electrocardiogram, airflow measured qualitatively by an oral-nasal thermistor and respiratory effort measured by thoracoabdominal piezoelectric belts.

DETAILED DESCRIPTION OF THE INVENTION

The following abbreviations have been used in this application.

| | |
|---|---|
| AHI | apnea-hypopnea index |
| ASC | Associated Sleep Center |
| BMI | body mass index |
| CI | confidence intervals |
| CPAP | continuous positive airway pressure |
| CT | cumulative time |
| EEG | electroencephalogram |
| MARS | multivariate adaptive regression splines |
| OSA | obstructive sleep apnea |
| ROC | receiver operator characteristic |
| SE | standard error |
| VAMC | Veterans Affairs Medical Center |

References relevant to the invention are listed at the end of the specification.

The term Apopnea Hypopnea Index or AHI as used herein means as the number of apneas plus the number of hypopneas per hour.

The term delta index as used herein means the absolute deviation from the mean of the oxygen saturation measured at twelve second intervals.

The present invention provides a predictive tool for determining AHI from overnight pulse oximetry readings. From the AHI it can be diagnosed whether or not an individual has OSA. The development of the tool is based on a study in which it was observed that: 1) among the different oximetry indices, the delta index was the best predictor of the presence of OSA, although desaturation events provided similar levels of diagnostic accuracy, 2) the delta index had good sensitivity but low specificity, 3) a bootstrap aggregation of models involving a combination of all the oximetry indices (compared to using the delta index alone) improved the precision of the prediction of the AHI, and 4) the prediction model developed in this invention was validated in two independent sleep clinics. To our knowledge, there has been no previous study that has compared systematically the relative utility of the various quantitative indices derived from overnight oximetry in the diagnosis of OSA.

Figure 1:
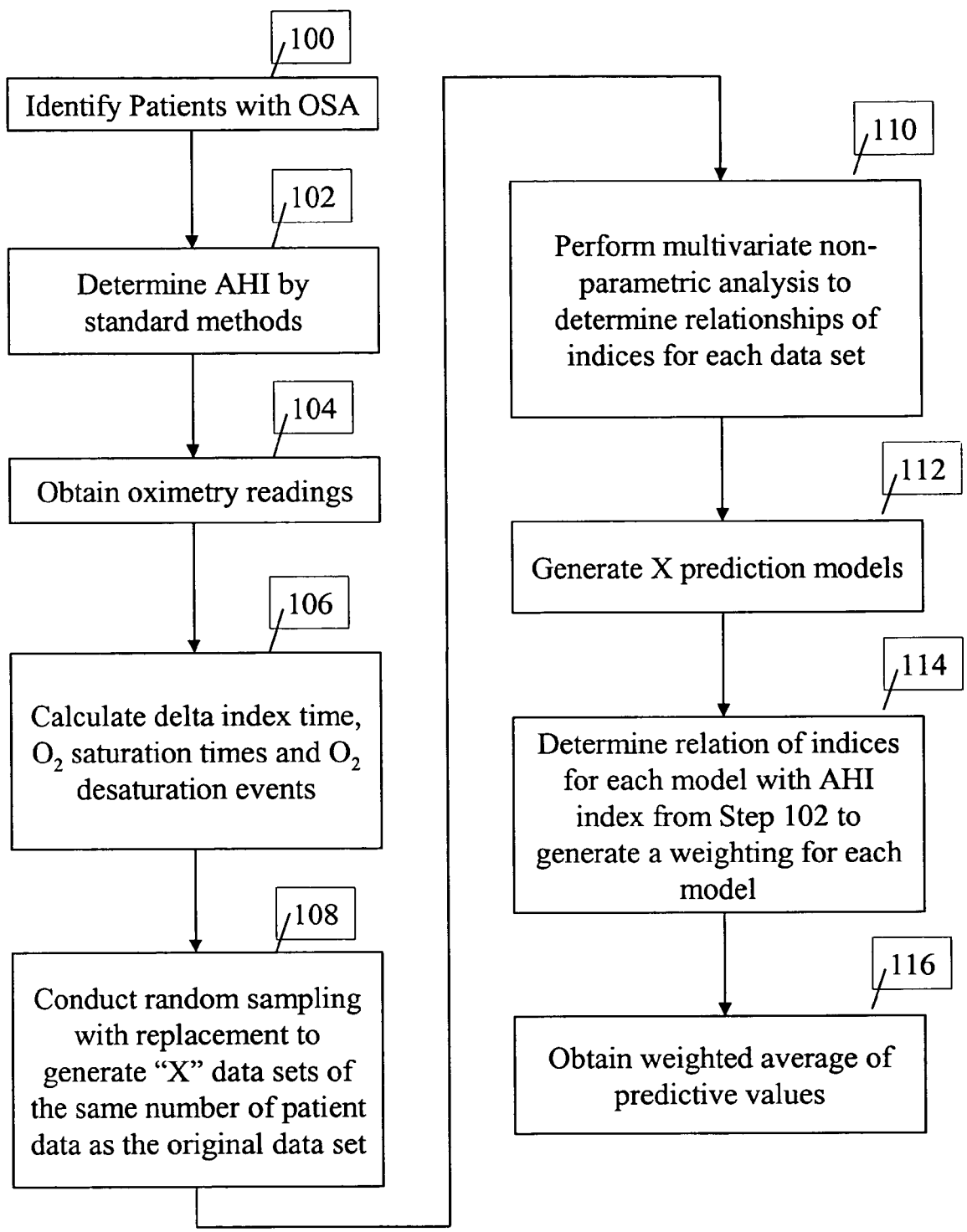
FIG. 1 is a representation of the steps for developing the predictive tool of the present invention.

To prepare the predictive tool of the present invention (FIG. 1), patients with OSA are identified (Step 100). For each individual, polysomnography (PSG) recordings are carried out, preferably overnight. Standard overnight PSG recordings include electroencephalogram (EEG) recordings, electro-oculogram and electromyogram (EMG). Airflow recordings and respiratory effort can also be recorded. During these recordings, sleep stages are scored in selected time epoch. Each epoch is analyzed and AHI is determined by standard parameters (Step 102). In an alternative embodiment, electrocardiogram readings may also be recorded.

During the PSG recordings, pulse oximetry readings are also obtained. For these recordings, a patient is connected to a pulse oximeter and overnight readings are obtained (Step 104). The pulse oximeter may be a portable unit. The oximeter probe is applied to the patient's finger overnight. The device can be turned off in the morning and the data mailed back to the health care facility for analysis. The data is downloaded from the pulse oximeter into a computer. Typically this is done in an ASCII format. Then the data is analyzed as described herein. The data is first checked for artifacts as described by Taha and colleagues (Taha et al., Sleep (1997), 20:991-1001) and then the total recording time, the delta index, the cumulative time spent under an oxygen saturation of selected percentages and the number of desaturation events at selected percentages are determined (Step 106). In one embodiment, the selected percentages for determining time spent under oxygen saturation are generally below a certain levels of oxygen saturation between the range of 50 to 100%. For example, time spent under oxygen saturation of 80, 81, 82, 83, 84, 85, 86, 87, 88, 89, 90, 91, 92, 93, 94, 95, 96, 97, 98, 99 and 100% can be determined. In one embodiment, the time spent under oxygen saturation of 80, 82, 84, 86, 88 and 90% is determined. For desaturation events, the level of desaturation may be selected from 2 to 20%. For example, in one embodiment, the level of desaturation is 2, 3 and 4%.

A sufficient number of random data sets are generated from the original data. Each of the random data sets utilize the process known as bootstrapping. This process allow for selection of random patients to fill a set of equal size to the original data set. However, each time a selection of a patient is made, the patient is then put back into the pool of available patients for the selection of the next patient. Therefore, it is possible the same patient may appear in the same data set multiple times or none at all. The ability to be able to derive many random sets from a limited number of available patients affords the mathematical flexibility necessary in the development of the model (Step 108). In one embodiment, the number of data sets generated in 20.

The data are then subjected to multivariate non-parametic analysis to determine relationships of indices in each data set (Step 110). This can be done by standard statistical methods or by using commercially available software (such as Multivariate Adaptive Regression Splines, Salford Systems, San Diego, Calif.). Multivariate adaptive regression splines (MARS) were used to develop prediction models. The splines consist of one or more of a series of linear segments joined at adjacent ends that could be fitted to nonlinear data. MARS is a multivariate nonparametric procedure that builds flexible regression like models using exhaustive search techniques to test necessity of different predictors. Interactions between independent variables are simultaneously tested. From these relationships, a prediction model is developed for each set (Step 112). The model is adaptive because it overfits the data, and then determines the size of the model that optimizes the tradeoff between accuracy (bias) and variance (precision) using a ten-fold cross-validation. The final model is obtained through backward elimination to the optimal model size. Predicted value is derived as linear combination of basic functions.

The various indices of overnight oximetry are correlated with each other. As a result, a model developed on the basis of the interrelationship of the indices is likely to depend upon the individual cases used to develop the model. To address this issue, a technique that uses an aggregated result from multiple models can be used (Breiman, Ann Stat (1996); 24:2350-83). A provisional predicted AHI value is obtained for each patient corresponding to each model and the provisional predicted AHI value is compared to the actual AHI value (determined by standard methods from the PSG recordings) to provide weight for the particular data set model (Step 114). The final predictive values can lie between 0 and 360/hr beyond which they are truncated at the midpoint value since values outside this range are unachievable. Based on the weight for each model, a weighted average for predictive values (the final AHI value) is obtained for each patient (Step 116). The plurality of predictive models as described herein (bootstrapping) and obtaining a weighted average of the predicted AHI values (bagging) provides a predictive tool for predicting AHI values in individuals. The prediction model can be validated by obtaining data from another group of patients or patients from another facility.

The aggregation method used herein results in a significant improvement of the precision of the predicted AHI. This improvement is important because even small improvements in precision can increase the confidence in the prediction. An advantage of the present method includes that it is potentially useful to identify severe OSA or confirm the absence of OSA; the instrumentation required for it is not expensive; and it can be performed in a patient's home.

Other advantages are that oximetry is a simple procedure so that a repeat test in the patient's home on a separate night in the event of technical difficulties would be reasonable. Portable oximeters capable of storing data over a prolonged recording are now readily available. The oximeter can be sent home with the patient and after the overnight recording, mailed back to the sleep laboratory or physician's office for downloading of the data and a computer generated report of the predicted AHI with its 95% confidence interval reported back to the physician through an automated system.

The clinical utility of pulse oximetry can be assessed quantitatively from the likelihood ratios. The Bayesian approach is to multiply the pre-test odds by the likelihood ratio to determine the post-test odds. Positive likelihood ratios that cause large changes in the likelihood of disease are >10, moderate changes 5 to <10, small changes 2 to <5 and trivial changes <2. The data presented in Example 1 show that pulse oximetry using the aggregated method can produce larger shifts in the pre-test to post-test certainty of predicting the probability of OSA in the normal and severe ranges of disease severity as compared to the mild to moderate range.

The present invention is also directed to a computational system including software storage devices such as a floppy disk, hard drive, a CD, a zip drive, flash card, smart drive etc. having thereon computer readable code for causing a computer to execute all or a substantial portion of diagnostic method using a predictive tool as described herein.

Figure 2:
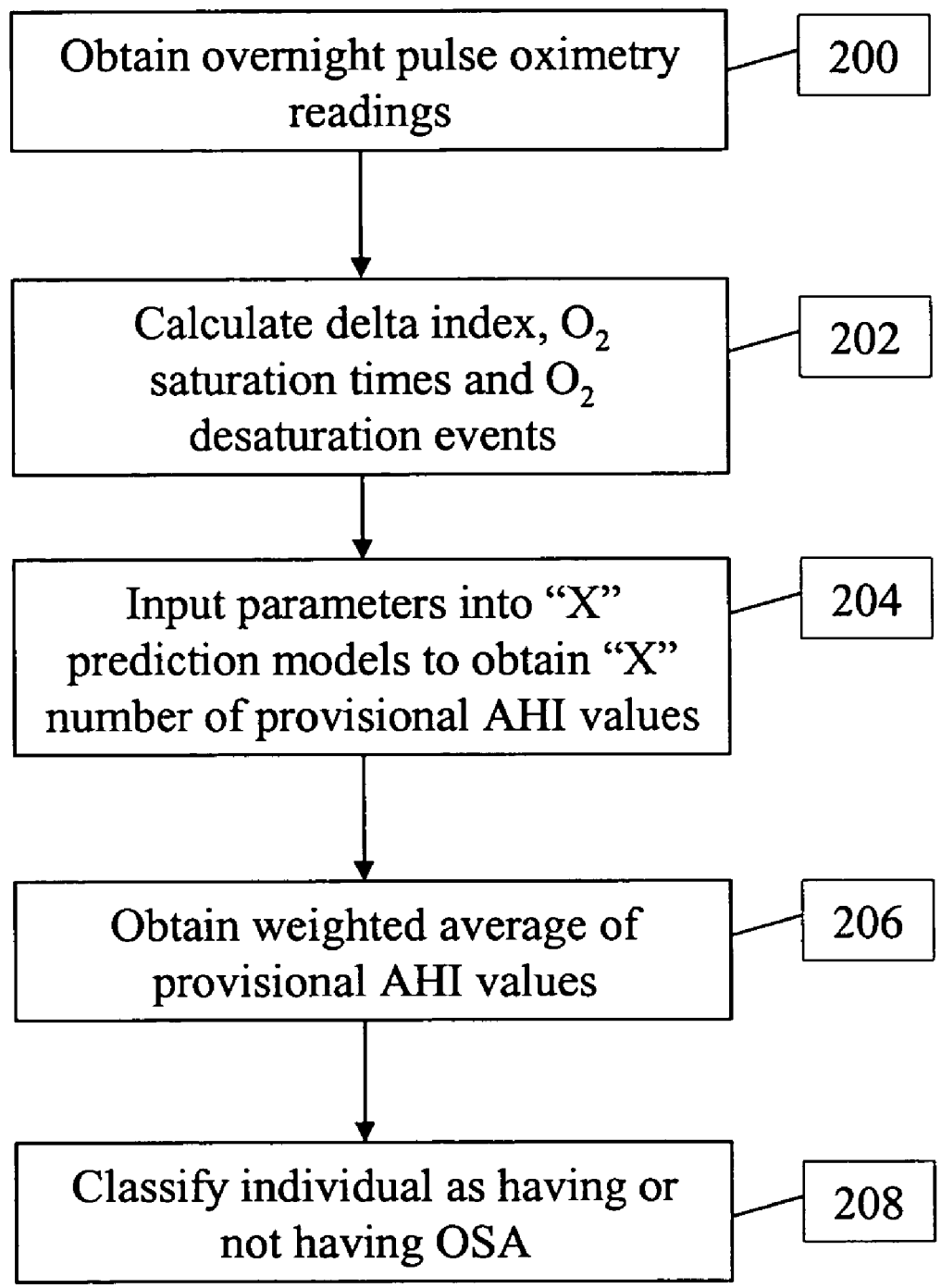
FIG. 2 is a representation of steps involved in classifying a patient as having OSA or not having OSA.

The present invention also provides a method of using the predictive tool for determination of AHI in a patient (FIG. 2). The method comprises obtaining pulse oximetry data from an individual (Step 200), preferably overnight, and calculating the delta index, time of $O_2$ saturation at selected percentages, and $O_2$ desaturation events (Step 202). In one embodiment, additional indices selected from the group consisting of: electroencephalogram (EEG), electro-oculogram, submental and bilateral leg electromyograms, electrocardiogram, airflow measured by an oral-nasal thermistor, respiratory effort measured by thoracoabdominal piezoelectric belts and responses to sleep history questionnaires may are obtained. These indices are used as input parameters for each prediction model of Step 112 in FIG. 1 to obtain a provisional AHI index (Step 204) for each model. A final AHI value is determined by averaging the weighted values from each model (Step 206). Based on the final predicted AHI value, an individual can be classified as having OSA or not having OSA (Step 208).

The invention is further described by the examples provided herein which are intended to be illustrative and should not be construed as being restrictive in any way.

EXAMPLE 1

Five hundred and sixteen patients suspected of having OSA were enrolled into this study. Patients were recruited from two independent sleep clinics in Buffalo, N.Y.: the Associated Sleep Center (ASC) and the Buffalo Veterans Affairs Medical Center (VAMC) Sleep Center. The eligibility criteria were all patients who underwent an overnight PSG for suspected sleep apnea. The exclusion criteria were age <18 years, the sleep study was done while on oxygen supplementation, or CPAP titration was performed on the same night as the diagnostic study (split-night study). Of the 516 patients, 224 were assigned to the Derivation Group, 101 to Validation Group I and 191 to Validation Group II. The patient characteristics of the Derivation and two Validation Groups are shown in Table 1.

TABLE 1

Summary of patient characteristics.

| Patient characteristics | Derivation Group n = 224 | Validation Group I n = 101 | Validation Group II n = 191 |
| --- | --- | --- | --- |
| Age (years) | 48.9 ± 12.3 | 51.8 ± 11.5 | 56.0 ± 12.8[§§] |
| BMI (kg/m$^2$) | 32.3 ± 7.4 | 32.7 ± 7.1 | 32.9 ± 8.7 |
| Neck circumference (cm) | 41.6 ± 4.5 | 42.6 ± 4.8 | 43.7 ± 4.2[§] |
| AHI (events/hour) | 18.2 ± 20.0 | 20.2 ± 19.5 | 18.2 ± 21.2 |
| AHI (events/hour) range | 0-108.6 | 0-92.1 | 0-147.2 |
| AHI <5/hour | 33.0% | 19.8% | 25.7% |
| AHI 5 to <15/hour | 23.2% | 33.7% | 35.6% |
| AHI 15 to <30/hour | 25.5% | 20.8% | 18.3% |
| AHI ≧30/hour | 18.3% | 25.7% | 20.4% |

Definition of abbreviations: BMI = body mass index; AHI = apnea-hypopnea index
Values represent mean ± standard deviation
[§§]significantly different from derivation group and validation group I (p < 0.05)
[§]significantly different from derivation group (p < 0.05)

All groups had similar body mass index (BMI) and AHI. The patients in Validation Group II were significantly older compared to the Derivation Group and Validation Group I, and had a larger neck circumference compared to the Derivation Group.

All patients underwent standard overnight PSG with recordings of electroencephalogram: (EEG), electro-oculogram, submental and bilateral leg electromyograms, and electrocardiogram. Airflow was measured qualitatively by an oral-nasal thermistor and respiratory effort by thoracoabdominal piezoelectric belts. All signals were collected and digitized on a computerized PSG system (ASC: Rembrandt, Aerosep Corp., Buffalo, N.Y.; Buffalo VAMC: Acquitron, Mallinckrodt, St. Louis, Mo.).

Sleep stages were scored in 30-sec epochs using standard criteria. Each epoch was analyzed for the number of apneas, hypopneas, EEG arousals, oxyhemoglobin desaturation, and disturbances in cardiac rate and rhythm. Apnea was defined as the absence of airflow for at least 10 seconds. Hypopnea was defined as a visible reduction in airflow lasting at least 10 seconds associated with either a 4% decrease in arterial oxyhemoglobin saturation or an EEG arousal. An arousal was defined according to the criteria proposed by the Atlas Task Force. Apneas and hypopneas were classified as obstructive if respiratory effort was present and central, if respiratory effort was absent during the event. The AHI was defined as the number of apneas and hypopneas per hour of sleep. Only one person in each sleep laboratory, blinded to the off line analysis of pulse oximetry data, scored the sleep studies.

Pulse oximetry data was collected as part of the PSG. Measurement of arterial oxyhemoglobin saturation was performed with a pulse oximeter (ASC: Nellcor N-200,Nellcor Puritan Bennett, St. Louis, Mo.; Buffalo VAMC: Biox 3740, Ohmeda, Boulder, Colo.). The oximeter probe was placed on the patient's finger. Oximetry data was digitized and collected at 8 and 10 Hz at the ASC and Buffalo VAMC, respectively, into a computerized PSG system along with the other sleep study parameters. The recording time was defined as lights-off to lights-on (approximately 10 p.m. to 6 a.m.). Recording time was used as the denominator for the various indices of overnight pulse oximetry rather than total sleep time since EEG is not be available when oximetry is to be utilized outside of the sleep laboratory. The oximeters in both sleep laboratories employed a moving average of 3 seconds. The oximetry data was then extracted from the computerized PSG system for further off line analysis. Oximetry data was averaged over two-second sampling intervals. Artifacts were removed by eliminating all changes of oxygen saturation between consecutive sampling intervals of greater than 4% per second, and any oxygen saturation less than 20%. The definition of a desaturation event was also based on the work of Taha and colleagues (Taha et al., Automated detection and classification of sleep disordered breathing from conventional polysomnography. Sleep 1997 20:991-1001). Every data point was examined sequentially to determine if criteria were met to define an event. The criteria for an event were a decrease of at least the set amount (2%, 3%, or 4%) in oxygen saturation from the initial data value for at least 10 sec, and at a rate greater than 0.1% sec. In addition, the oxygen saturation returned within 60 sec to within 1% of the initial value, or increase from its nadir by 1.5 times or more of the set amount of the dip. Once the criteria were met, a new search for an event was initiated at the next data point after the event. The delta index was calculated as the average of absolute differences of oxygen saturation between successive 12-sec intervals (sum of the absolute differences between two successive points, divided by the number of intervals measured). The index quantifies oxygen saturation variability. In OSA, oxygen desaturation events associated with respiratory events cause fluctuations in the oxygen saturation signal leading to high delta index values. A total of 10 indices were calculated for each patient in the Derivation Group. The delta index, number of desaturation events (to 2%, 3% and 4% levels) per hour of recording time, and the cumulative time (CT) spent below 90, 88, 86, 84, 82,and 80% saturation as a proportion of total recording time.

The various indices of overnight pulse oximetry (predictor variables) were subjected to multivariate non-parametric analysis. The prediction equation using the delta index alone derived using the multivariate model in the Derivation Group is:

$$\log_{10}(AHI+1)=1.306+0.269*BF1-2.316*BF2 \quad \text{(equation 1)}$$

where BF1 is the maximal value of either zero or (DX-0.57), BF2 is the maximal value of either zero or (0.570-DX), and DX is the delta index. The coefficient of determination ($r^2$) between the actual and predicted AHI was 0.60 using this initial multivariate prediction model involving the delta index alone.

To minimize the effect of differences in the correlation of various indices in different individuals, the predictions of different plausible models (representing different interrelationships between indices) were averaged as described above. Bootstrap aggregation model averaging ("Bagging") was used by developing 20 random samples (with replacement) from the original data set. Each of the twenty data sets has the same size as the original derivation data set. Because random sampling with replacement was used, a particular patient could occur more than once in any of the twenty generated data sets, and some may not appear at all. For each of the 20 data sets, a MARS model was generated in a similar form to that shown in equation 1.

For every patient in original derivation data set (subscript i), and each of predictive models (subscript m), the predicted value of $AHI0 \leq p_{i,m} \leq 360$, was determined, so that every patient was assigned 20 predictions. Predictions beyond this range were truncated at the endpoint values because results outside this range are unachievable. The maximal value 360/hr would indicate continuous apnea since apnea is defined as an event of 10 sec or more in duration.

The multiple linear regression model with bootstrap sample predictions as independent variables was fitted to transformed response:

$$\log_{10}(AHI+1)=b_0+b_1p_1 \ldots +b_{20}p_{20}+e \quad \text{(equation 2)}$$

wherein AHI was measured for that patient by overnight polysomnography and e is the error term. The best regression model was found with all subsets method. If the model was not included in the final regression model, the corresponding coefficient was assigned to be zero. Weighted average of the predictions was used to obtain a single aggregated prediction of AHI for a particular patient:

$$\log_{10}(AHI+1)=\Sigma(b_m*p_m)/\Sigma b_m \quad \text{(equation 3)}$$

Figure 3:
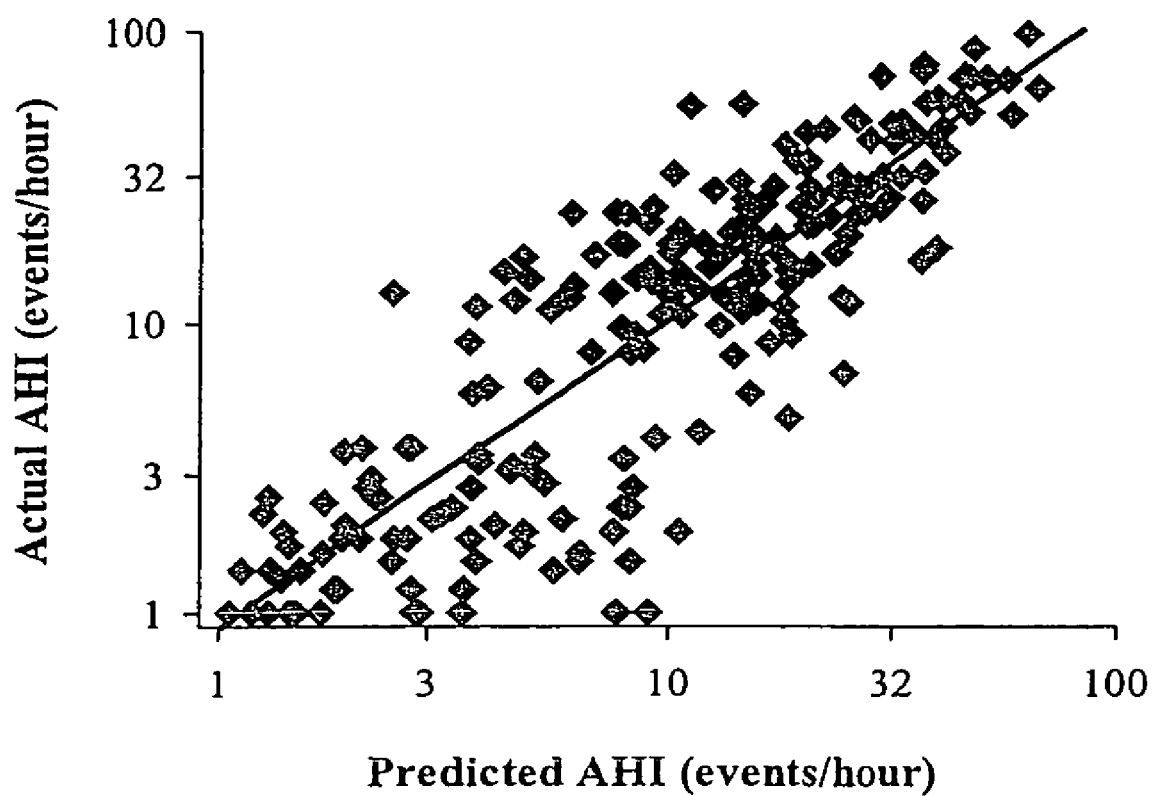
FIG. 3 is a representation of the aggregated model using a combination of all ten oximetry indices to predict the AHI from the derivation group (n=224). The predicted and actual AHI values are shown on logarithmic scale. The coefficient of determination ($r^2$) between the actual and predicted AHI was 0.70 which is significantly improved compared to 0.60 (data not shown) using the initial model ($p<0.05$).

The aggregated model using a combination of the various oximetry indices increased the $r^2$ between the actual and predicted AHI ($r^2=0.70$) which was significantly higher than the initial model (p<0.05) as derived by equation 1. The predicted and actual AHI of the 224 patients in the Derivation Group using the aggregated model are shown in FIG. 3. In comparison with the derivation model using only the delta index, there was an improvement in terms of diagnostic accuracy using $\geq 15$/hr to define OSA with the aggregated model. The area under the ROC curve was increased to 0.9±0.02 with a sensitivity of 90% (CI: 82-95%) and a specificity of 70% (CI: 62-78%) using the aggregated model. The term "sensitivity" as used herein refers to the true positive rate and the term "specificity" as used herein refers to the true negative rate.

The prediction model developed from the Derivation Group as described herein was validated in two independent facilities (Validation Group I and Validation Group II). The characteristics of the patients in the Derivation and two Validation Groups were compared using nonparametric oneway analysis of variance. If a significant difference was found, a multiple comparison procedure (Dunn's method) was used to determine a source of the difference (Sigmastat, SPSS Inc., San Rafael, Calif.). In Validation Group I, the actual AHI values of 92 out of 101 patients were within the CI of the predictions for the AHI using the aggregated model. The proportion of patients within the confidence interval of the prediction was 90% (CI: 83-95%). In Validation Group II, actual AHI values of 174 out of 191 patients were within the CI of the predicted AHI. The proportion of patients within the confidence interval of the prediction was 91% (CI: 86-95%).

Figure 4:
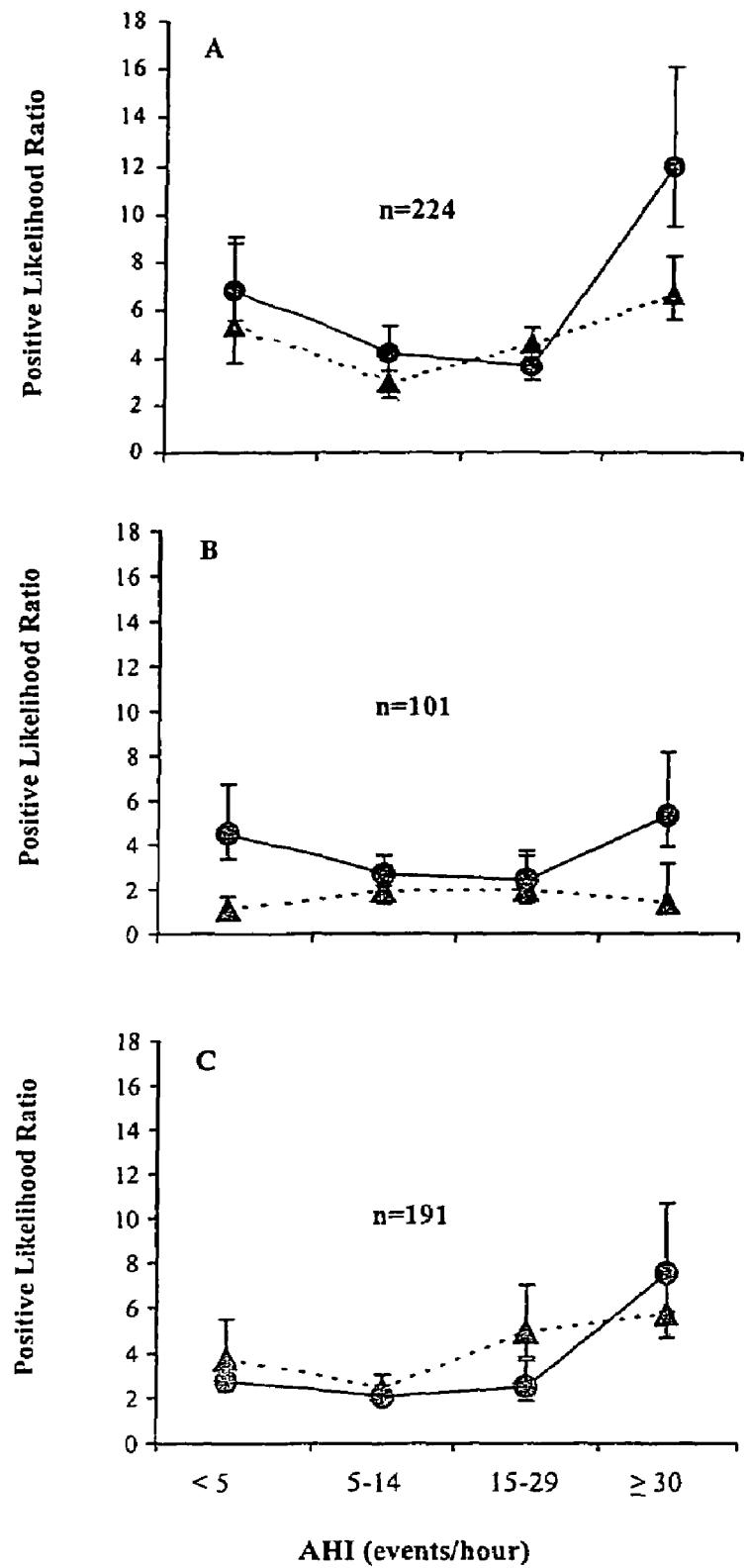
FIG. 4 is a representation of the positive likelihood ratios (±SE) in: A) Derivation Group, B) Validation Group I, and C) Validation Group II according to the severity of the AHI derived from multivariate prediction models using the delta index alone (filled triangles) versus the aggregated model (filled circles). The aggregated model improved the prediction mainly at both ends of the AHI spectrum (<5/hour and ≧30/hour).

To determine exactly at what levels of disease severity the delta index model and the aggregated model differed, we stratified the data into four groups according to the AHI measured by PSG: normal (AHI<5/hr), mild (5-<15/hr), moderate (15-<30/hr) and severe ($\geq$30/hr). FIG. 4 shows the positive likelihood ratios in all patient groups according to the severity of the AHI of the multivariate prediction models using the delta index alone versus the aggregated model. Both the delta index and the aggregated models improved the prediction mainly at both ends of the AHI spectrum (<5/hour and $\geq$30/hour). The aggregated model was superior to the delta index model in the severe level in the Derivation Group and the severe level and normal level in Validation Group I, but no different in Validation Group II (FIG. 4).

The likelihood ratios are computed from the post test probability divided by the pre test probability and produce an indicator to assist the physician in determining the presence or absence of OSA in an individual patient. The likelihood ratios for the aggregated model in the Derivation Group were 6.9 (95% CI: 4.4-10.8), 4.3 (95% CI: 2.8-6.5), 3.6 (95% CI: 2.5-5.4) and 12 (95% CI: 7.1-20) for normal, mild, moderate and severe disease severity respectively. The likelihood ratios fell within the 95% CI for the normal and mild levels in Validation Group I and for the moderate and severe levels in Validation Group II (FIG. 4). The likelihood ratios for the delta index model in the Derivation Group were 5.4 (95% CI: 2.2-12.6), 2.5 (95% CI: 1.7-5.3), 3.0 (95% CI: 2.1-4.4) and 4.0 (95% CI: 3.6-6.5) for normal, mild, moderate and severe disease severity respectively. The likelihood ratios fell within the 95% CI for the mild level only in Validation Group I and for all levels in Validation Group II (FIG. 4).

To obtain an overall estimate, we combined the results from the Derivation and both Validation Groups for the aggregated model. The overall likelihood ratios for the aggregated model in the Derivation Group were 4.2 (95% CI: 3.3-15.3), 3.4 (95% CI: 2.7-4.3), 3.0 (95% CI: 2.2-4.1) and 6.7 (95% CI: 4.9-9.2) for normal, mild, moderate and severe disease severity respectively. The overall likelihood ratios for the delta index were 3.3, 2.5, 3.0 and 4.9/hr for normal, mild, moderate and severe disease severity respectively. Therefore, the likelihood ratios were at the lower 95% CI in both the normal and severe levels of disease severity.

A recent study using an automated analysis of oximetry data and a desaturation event definition of $\geq$4% lower than baseline, reported a very high sensitivity of 98% and specificity of 88%. However, this study used a definition of arousals that differs substantially from the criteria proposed by the Atlas Task Force that has come into general use in the United States. As a result, their definition of hypopnea will differ substantially from ours. These investigators found that the addition of arousal-based scoring criteria (using their definition of arousal) for hypopnea causes only small changes in the AHI. However, a large study has found that incorporating arousals based on the Atlas Task Force criteria on the hypopnea definition do impact on the value of the AHI. Table 2 shows the comparison of our results to others using an AHI cut-off value of $\geq$15 events/hour to define the presence of OSA. Our results are consistent with others in the field although our specificity was higher using the aggregated model compared to the previously published studies using the delta index.

The study by Levy and colleagues reported that the correlation between the delta index and actual AHI was 0.72, whereas in Olson's study the Spearman's correlation coefficient between the delta index and actual AHI was 0.71. In our study, the correlation (expressed as Pearson's correlation) between the predicted and actual AHI was 0.77, which improved to 0.83 when we used a combination of the oximetry indices. Therefore, our prediction model provides an improvement compared to using a simple regression between the delta index alone and actual AHI.

TABLE 2

Comparison to the results of others.

| Study | Method used | Sensitivity % (CI)* | Specificity % (CI)* |
|---|---|---|---|
| Vazquez et. al. | 4% desaturation | 98 | 88 |
| Levy et. al. | delta index $\geq$0.6 | 98 (96-100) | 46 (37-55) |
| Olson et. al. | delta index $\geq$0.4 | 88 | 40 |
| Present study | 4% desaturation | 94 (87-98) | 44 (35-52) |
|  | delta index $\geq$0.63 | 91 (84-95) | 59 (49-69) |
|  | AHI predicted from aggregated model | 90 (82-95) | 70 (62-78) |

*based on an AHI cut off value $\geq$15 events/hour
CI = 95% confidence interval While this invention has been described through specific embodiments, routine modifications will be apparent to those skilled in the art and such modifications are intended to be within the scope of the present invention.

References

1. Agency for Health Care Policy and Resarch (AHCPR), Department of Health and Human Services, U.S. Public Health Service. Systematic review of the literature regarding the diagnosis of sleep apnea. Summary, evidence report/technology assessment number 1. AHCPR Publication 99-E002, February 1999.
2. Gyulay S, Olson L G, Hensley M J, et al. A comparison of clinical assessment and home oximetry in the diagnosis of obstructive sleep apnea. Am Rev Respir Dis 1993; 147:50-53.
3. Levy P, Pepin J L, Deschaux-Blanc C, et al. Accuracy of oximetry for detection of respiratory disturbances in sleep apnea syndrome. Chest 1996; 109:395-99.
4. Choi S, Bennett L S, Mullins R, et al. Which derivative from overnight oximetry best predicts symptomatic response to nasal continuous positive airway pressure in patients with obstructive sleep apnea? Respir Med 2000; 94:895-99.
5. Jaeschke R, Guyatt G H, Sackett D L. Users' guides to the medical literature. III. How to use an article about a diagnostic test. B. What are the results and will they help me in caring for my patients? The Evidence-Based Medicine Working Group. JAMA 1994; 271:703-7.
6. Olson L G, Ambrogetti A, Gyulay S G. Prediction of sleep-disordered breathing by unattended overnight oximetry. Journal of Sleep Research 1999; 8:51-5.

7. Vazquez J, Tsai W H, Flemons W W, et al. Automated analysis of digital oximetry in the diagnosis of obstructive sleep apnea. Thorax 2000; 55:302-307.
8. Taha B H, Dempsey J A, Weber S M, et al. Automated detection and classification of sleep-disordered breathing from conventional polysomnography data. Sleep 1997; 20:991-1001.
9. Friedman J H. Multivariate adaptive regression splines (with discussion). Annals of Statistics 1991; 19:1-141.
10. Breiman L. The heuristics of instability in model selection. Ann Stat 1996; 24:2350-83.
11. Hanley J A, McNeil B J. The meaning and use of the area under the receiver operating characteristics (ROC) curve. Radiology 1982; 143:29-36.
12. El-Solh A A, Grant B J B. A comparison of severity of illness scoring systems for critically ill obstetric patients. Chest 1996; 110: 1299-1304.
13. El-Solh A A, Ten-Brock E, Shucard D W, et al. Validity of Neural Network in Sleep Apnea. Sleep 1999; 22:105-111.
14. Flemons W W, Whitelaw W A, Brant R, Remmers J E. Likelihood ratios for a sleep apnea clinical prediction rule. Am J Respir Crit Care Med 1994; 150:1279-1285.
15. Loube D I, Gay P C, Strohl K P, et al. Indications for positive airway pressure treatment of adult obstructive sleep apnea patients: a consensus statement. Chest 1999; 115:863-6.

The invention claimed is:

1. A method for predicting respiratory disturbances in an individual comprising the steps of:
 a) identifying patients having obstructive sleep apnea;
 b) determining actual Apopnea Hypopnea Index (AHI) in the patients;
 c) obtaining pulse oximetry recordings from the patients;
 d) determining patient data comprising a set of indices from the pulse oximetry readings comprising: delta index, time spent at selected oxygen saturation levels and oxygen desaturation events;
 e) performing random sampling with replacement of patient data from (d) to generate a plurality of data sets;
 f) performing multivariate non-parametric analysis in the plurality of data sets to generate a plurality of prediction models;
 g) obtaining a provisional predictive AHI value for each patient corresponding to each prediction model;
 h) comparing the provisional predictive AHI value to actual AHI value for each patient to provide weight to each prediction model; and
 i) providing each prediction model to a health care professional,
 wherein the plurality of prediction models and weight of the prediction models provides a predictive tool for predicting respiratory disturbances in an individual.

2. The method of claim 1 further comprising the step of validating the prediction models.

3. The method of claim 1, wherein the pulse oximetry readings are obtained overnight.

4. The method of claim 1, wherein the selected oxygen saturation is in the range of 50 to 100%.

5. The method of claim 4, wherein the selected oxygen saturation levels are selected from the group consisting of 80, 81, 82, 83, 84, 85, 86, 87, 88, 89, 90, 91, 92, 93, 94, 95, 96, 97, 98, 99% and combinations thereof.

6. The method of claim 5, wherein the selected oxygen saturation levels are 80, 82, 84, 86, 88 and 90%.

7. The method of claim 1, wherein the oxygen desaturation levels for desaturation events are selected from the group consisting of 2, 3, 4, 5, 6, 7, 8, 9, 10, 11, 12, 13, 14, 15, 16, 17, 18, 19, 20% and combinations thereof.

8. The method of claim 7, wherein the oxygen desaturation levels are 2, 3 and 4%.

9. The method of claim 1 further comprising:
 a) obtaining additional indices in claim 1 (c) selected from the group consisting of:
 electroencephalogram (EEG), electro-oculogram, submental and bilateral leg electromyograms, electrocardiogram, airflow measured by an oral-nasal thermistor, respiratory effort measured by thoracoabdominal piezoelectric belts and responses to sleep history questionnaires; and
 b) utilizing the additional indices in the step of claim 1 (e).

10. A method for predicting respiratory disturbances in an individual comprising the steps of:
 a) identifying patients having obstructive sleep apnea;
 b) determining actual Apopnea Hypopnea Index (AHI) in the patients;
 c) obtaining pulse oximetry recordings from the patients;
 d) determining patient data comprising a set of indices from the pulse oximetry readings comprising: delta index, time spent at selected oxygen saturation levels and oxygen desaturation events;
 e) performing random sampling with replacement of patient data from (d) to generate a plurality of data sets;
 f) performing multivariate non-parametric analysis in the plurality of data sets to generate a plurality of prediction models;
 g) obtaining a provisional predictive AHI value for each patient corresponding to each prediction model;
 h) comparing the provisional predictive AHI value to actual AHI value for each patient to provide weight to each prediction model;
 i) obtaining pulse oximetry recordings from the individual;
 j) determining a set of indices from the oximetry readings comprising, delta index, time spent at selected oxygen saturation levels and oxygen desaturation events;
 k) subjecting the set of indices to the plurality of prediction models to obtain a plurality of provisional predicted AHI values corresponding to each model;
 l) obtaining a final predicted AHI value by averaging the weighted provisional predicted AHI values; and
 m) providing each prediction model to a health care professional;
 wherein the plurality of prediction models and weight of the prediction models provides a predictive tool for predicting respiratory disturbances in an individual.

11. The method of claim 10, wherein the pulse oximetry readings are obtained overnight.

12. The method of claim 10, wherein the selected oxygen saturation is in the range of 50 to 100%.

13. The method of claim 12, wherein the selected oxygen saturation levels are selected from the group consisting of 80, 81, 82, 83, 84, 85, 86, 87, 88, 89, 90, 91, 92, 93, 94, 95, 96, 97, 98, 99% and combinations thereof.

14. The method of claim 13, wherein the selected oxygen saturation levels are 80, 82, 84, 86, 88 and 90%.

15. The method of claim 10, wherein the oxygen desaturation levels for desaturation events are selected from the group consisting of 2, 3, 4, 5, 6, 7, 8, 9, 10, 11, 12, 13, 14, 15, 16, 17, 18, 19, 20% and combinations thereof.

16. The method of claim 7, wherein the oxygen desaturation levels are 2, 3 and 4%.

17. The method of claim 10, further comprising the step of classifying an individual as having or not having obstructive sleep apnea based on the final predicted AHI value.

18. The method of claim 10, wherein step a) further comprises obtaining additional indices selected from the group consisting of: electroencephalogram (EEG), electro-oculogram, submental and bilateral leg electromyograms, electrocardiogram, airflow measured by an oral-nasal thermistor, respiratory effort measured by thoracoabdominal piezoelectric belts and responses to sleep history questionnaires; and step c) further comprises inputting the additional indices into the prediction models to obtain the provisional predicted AHI values.

19. A computational system for predicting respiratory disturbances, the system having software thereon to execute the steps comprising:
   a) receiving pulse oximetry readings;
   b) calculating indices comprising: delta index, time spent at selected oxygen saturation levels and oxygen desaturation events;
   c) subjecting the indices to a plurality of Apopnea Hypopnea Index (AHI) prediction models to generate provisional AHI values corresponding to each prediction model wherein each prediction model has specific weight assigned thereto;
   d) calculating a final AHI value based on a weighted average of the provisional AHI value; and
   e) providing the final AHI value to a health care professional.

20. The computational system described in claim 19, wherein:
   a) time spent at select oxygen saturation levels is selected from the group consisting of 80, 81, 82, 83, 84, 85, 86, 87, 88, 89, 90, 91, 92, 93, 94, 95, 96, 97, 98, 99% and combinations thereof; and
   b) oxygen desaturation levels for desaturation events are selected from the group consisting of 2, 3, 4, 5, 6, 7, 8, 9, 10, 11, 12, 13, 14, 15, 16, 17, 18, 19, 20% and combinations thereof.

21. The computational system of claim 19 further comprising software wherein step a) receives additional indices selected from the group consisting of: electroencephalogram (EEG), electro-oculogram, submental and bilateral leg electromyograms, electrocardiogram, airflow measured by an oral-nasal thermistor, respiratory effort measured by thoracoabdominal piezoelectric belts and responses to sleep history questionnaires; and step c) subjects the additional indices to the prediction models.

22. A computational system for predicting respiratory disturbances, the system having software thereon to execute the steps comprising:
   a) receiving indices comprising: delta index, time spent at selected oxygen saturation levels and oxygen desaturation events;
   b) subjecting the indices to a plurality of AHI prediction models to generate provisional AHI values corresponding to each prediction model wherein each prediction model has specific weight assigned thereto;
   c) calculating a final AHI value based on a weighted average of the provisional AHI value; and
   (d) providing the final AHI value to a health care professional.

23. The computational system of claim 22, wherein:
   a) time spent at select oxygen saturation levels is selected from the group consisting of 80, 81, 82, 83, 84, 85, 86, 87, 88, 89, 90, 91, 92, 93, 94, 95, 96, 97, 98, 99% and combinations thereof; and
   b) oxygen desaturation levels for desaturation events are selected from the group consisting of 2, 3, 4, 5, 6, 7, 8, 9, 10, 11, 12, 13, 14, 15, 16, 17, 18, 19, 20% and combinations thereof.

24. The computational system of claim 22 further comprising software wherein step a) receives additional indices selected from the group consisting of: electroencephalogram (EEG), electro-oculogram, submental and bilateral leg electromyograms, electrocardiogram, airflow measured by an oral-nasal thermistor, respiratory effort measured by thoracoabdominal piezoelectric belts and responses to sleep history questionnaires; and step c) subjects the additional indices to the prediction models.

* * * * *

UNITED STATES PATENT AND TRADEMARK OFFICE
CERTIFICATE OF CORRECTION

| | |
|---|---|
| PATENT NO. | : 7,309,314 B2 |
| APPLICATION NO. | : 10/947983 |
| DATED | : December 18, 2007 |
| INVENTOR(S) | : Brydon J. B. Grant et al. |

It is certified that error appears in the above-identified patent and that said Letters Patent is hereby corrected as shown below:

Title page, item (73), the Assignees' names should read:
--U.S. Department of Veterans Affairs, Washington, DC (US);
The Research Foundation of State University of New York,
Amherst, NY (US)--

Signed and Sealed this

Tenth Day of June, 2008

JON W. DUDAS
*Director of the United States Patent and Trademark Office*